United States Patent [19]

Lieber et al.

[11] Patent Number: 4,570,641

[45] Date of Patent: Feb. 18, 1986

[54] SURGICAL MYOMETER METHOD

[75] Inventors: Richard L. Lieber, Cardiff-By-The-Sea; Ronald J. Baskin, Davis, both of Calif.

[73] Assignee: The Regents of the University of California, Berkeley, Calif.

[21] Appl. No.: 614,941

[22] Filed: May 29, 1984

[51] Int. Cl.⁴ .............................................. A61N 5/06
[52] U.S. Cl. ................................ 128/774; 33/125 A; 356/355
[58] Field of Search ............... 128/774, 303 R, 303.1, 128/664, 665; 356/354–356; 33/125 A

[56] References Cited

U.S. PATENT DOCUMENTS 3,623,815  11/1971  Fontanel ........................ 356/354
3,954,337   5/1976  Ragland, Jr. ................... 356/355
4,008,964   2/1977  Plöckl ............................ 356/355
4,009,965   3/1977  Pryor ............................. 356/355

OTHER PUBLICATIONS

Koedam, "Determination of Small Dimensions by Diffraction of a Laser Beam", vol. 27, 7/1966.

Primary Examiner—Lee S. Cohen
Assistant Examiner—Steven Falk
Attorney, Agent, or Firm—Fitch, Even, Tabin & Flannery

[57] ABSTRACT

A method for optimizing length in a detached striated muscle being surgically reattached. The method includes illuminating a bundle of fibers in the muscle to produce a diffraction pattern related to sarcomere spacing in the fibers. Prior to surgical reattachment, the muscle is stretched to an optimal length, an evidenced by a preselected spacing between a pair of different-order diffraction lines in the diffraction pattern.

8 Claims, 4 Drawing Figures

SURGICAL MYOMETER METHOD

BACKGROUND OF THE INVENTION

The present invention relates to a method for determining the optimal muscle length in a detached skeletal muscle.

Surgical reattachment of a detached muscle to a selected anatomical site is an important procedure in human and veterinary orthopaedic surgery. Surgical reattachment of a muscle may be required in cases of severe muscle injury, where an injured muscle must be removed, and the movement controlled by the injured muscle is to be partially restored by repositioning a healthy muscle. A muscle reattachment operation may also be required in the course of treatment of certain neuromuscular diseases, which are characterized by severe muscular contraction. One method of treatment is to detach the contracted muscle or muscles temporarily, followed by a later surgical reattachment.

It is important in a muscle reattachment operation to place the detached muscle at an optimal length with respect to the positions of the skeletal attachment members. This is because skeletal muscles have an inherent optimal length, with respect to the positions of the controlled skeletal members, which allows for optimal force-generation and functional range of the muscles. This optimal length is one in which the muscles are only slightly stretched when the skeletal members are in a neutral position, i.e., the approximate position assumed by the skeletal members in the middle of their total range of motion. At either a suboptimal length, where the muscle is in a relatively slack condition, or at an overly stretched condition, the muscular strength and functional range is significantly reduced.

From the foregoing, the importance of surgically reattaching a detached muscle at an optimal muscle length can be appreciated. Heretofore, orthopaedic surgeons have relied upon "feel" to determine when a muscle is at an optimal length, such occurring when the muscle is stretched just beyond a slack condition. This approach is not always satisfactory due to a number of factors which can mislead the surgeon. In particular, since the muscle being reattached is composed both of elastic connective tissue and contractile muscle components, both the elasticity of the connective tissue and tension of the muscle components will contribute to the overall muscle tension which is sensed. Because of the elasticity of the connective tissue, the muscle may be stretched too tight by the time the surgeon begins to feel tension. The amount of overstretching is typically one-half inch or more beyond optimal length.

It is a general object of the invention, therefore, to provide a simple and accurate method for determining optimal muscle length in a surgical operation involving reattachment of a detached striated muscle.

It is yet another object of the invention to provide such a method which uses reliable and relatively inexpensive components.

SUMMARY OF THE INVENTION

The method of the invention includes first, illuminating a group of fibers in a detached muscle with a coherent light. The muscle fiber subunits, or sarcomeres, act as a diffraction grating to produce a diffraction pattern whose line-spacing is related to sarcomere length in a predictable way. The invention takes advantage of the observed feature in skeletal muscles that optimal length in a muscle corresponds to a particular sarcomere length which is quite similar for all skeletal muscles in human and veterinary animals. By measuring the diffraction-line spacing in the diffraction pattern of the illuminated muscle, the muscle can be pulled until a selected line-spacing corresponding to optimal sarcomere and muscle length is achieved.

In one embodiment of the invention, the diffraction line spacing is measured by projecting the muscle diffraction pattern against a detector having a plate-like viewing surface which is positioned a predetermined distance with respect to the illuminated muscle. Optimal muscle length is achieved by adjusting overall muscle length until the first-order diffraction line is a selected distance from the zero-order line on the viewing surface. In a second embodiment, the diffraction line spacings are measured by a electro-optical detector which includes an array of photodiodes operatively connected to a microprocessor. The detector functions to convert diffraction line patterns impinging on the array directly into sarcomere-length values.

These and other objects and features of the present invention will become more fully apparent when the following detailed description of the invention is read in conjunction with the accompanying drawings.

DETAILED DESCRIPTION OF THE INVENTION

Figure 1:
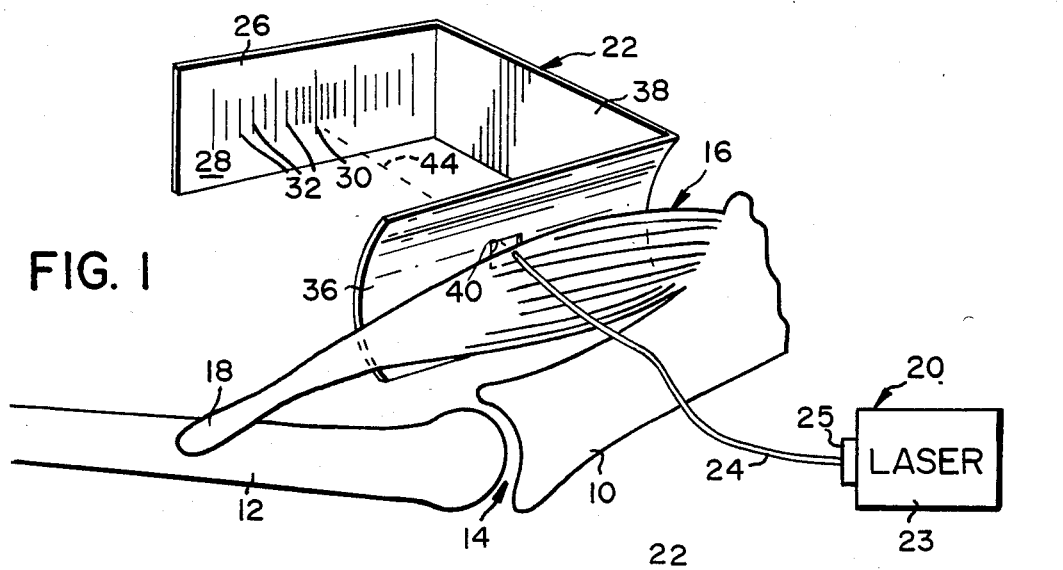
FIG. 1 depicts, somewhat schematically, an application of the method of the invention in determining the optimal length of a striated muscle.

FIG. 1 illustrates basic anatomical features encountered in the practice of the present invention. The features shown include a pair of skeletal bones 10, 12 which are connected at a movable axial joint indicated at 14. In the particular illustration, bone 12 is a so-called mobile skeletal bone capable of swinging movement about joint 14 with respect to fixed bone 10. A striated muscle 16 is connected at its opposite ends to the two bones by tendons, such as tendon 18 connecting the muscle to bone 12. It can be appreciated from the figure that contraction of muscle 16 acts to raise bone 12 upwardly about joint 14. The two bones, of course, are also connected by several other muscles which either augment the action of muscle 16 or act to move bone 12 in the opposite direction with respect to bone 10.

The particular muscle illustrated in FIG. 1 has a generally longitudinal architecture in which the muscle fibers making up the muscle extend substantially in the direction of the length of the muscle. However, it is understood that the present invention is applicable to surgical muscle attachment procedures in which the muscles having one of a number of different kinds of architecture, such as a pinnate architecture, in which the fibers making up a muscle have a feather-type pattern with respect to a muscle's long axis, or a radial architecture, in which the muscle fibers radiate outwardly from a central longitudinal axis. Also, the muscle may be one which is attached to two adjacent relatively movable bones, such as bones 10, 12, shown in FIG. 1, or may connect bones which themselves are separated by a third, intermediate skeletal member. The muscle may be one which produces predominantly joint-angle movement, such as the one illustrated in FIG. 1, or one whose contraction produces predominantly rotational movement of a bone about its long axis. The microstructure of a muscle, such as muscle 16, which is relevant to an understanding of the present invention, and which allows the general principles of the invention to apply to the surgical reattachment of virtually any skeletal muscle in man and veterinarian animals, will be described below.

Figure 2:
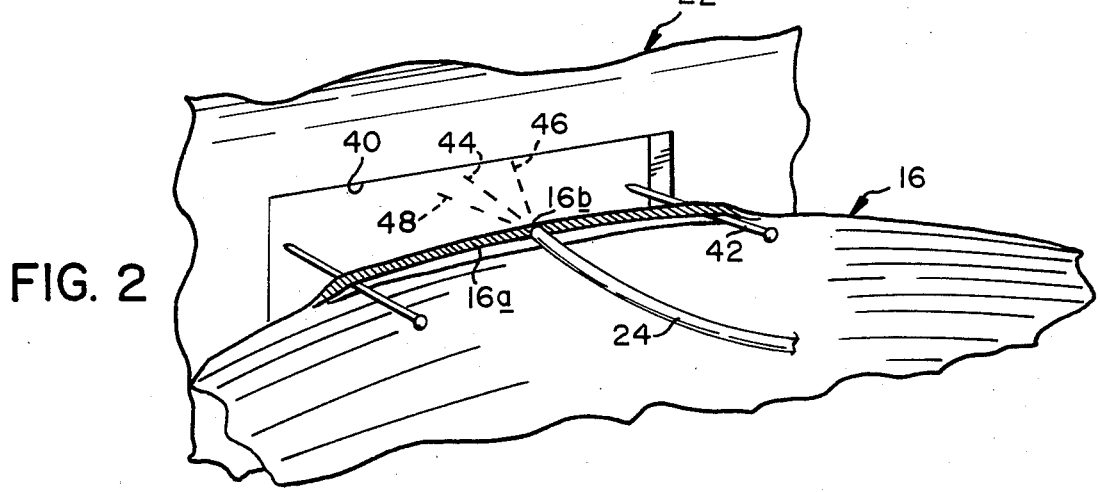
FIG. 2 is an enlarged view taken illustrating particularly the illumination of a small bundle of isolated fibers in a striated muscle.

With continued reference to FIG. 1, apparatus for carrying out the present invention generally includes a monochromatic light source 20 and a detector 22 which is used for detecting diffraction-line spacings in a diffraction pattern produced by illuminating a bundle of muscle fibers with source 20. Source 20 includes a conventional visible-light laser 23 having a power output of less than about 5 mW, such as laser Model No. 05-LHR-151, produced by Melles-Grillot (Irvine, Calif.). Source 20 further includes a fiber-optic probe 24, the end of which is adapted to be placed against the muscle or more particularly, against isolated fibers thereof, as shown in FIG. 2. Probe 24 preferably includes a fiber-bundle probe having a bundle diameter of about 0.125 inches, and outer-sheath diameter of about 0.230 inches and a length of about 3 feet. The probe should be sterilizable, e.g., by autoclaving. The fiber-bundle probe Model No. 7167, produced by Oriel (Stamford, Conn.), which transmits light in the range 400–1300 nm is suitable. The laser is equipped with a fiber optic hood 25 used to reduce the effect of ambient light, and to align the probe with the laser beam. Fiber optic hood Model No. 7144, manufactured by Oriel, is suitable.

With continued reference to FIG. 1, detector 22 includes a screen or plate 26 which is preferably formed of an opaque material which allows visible-light diffraction lines incident on its inner viewing surface 28 (the surface seen in FIG. 1) to be easily visualized. The width of the viewing surface is typically between about 2 and 5 centimeters and, its length, between about 6 and 10 centimeters. A series of parallel, vertical markings are formed on the plate's viewing surface, as shown. These markings include a central marking 30, and a series of markings, such as markings 32, which are calibrated to indicate sarcomere length according to the positions of zero-order and first order muscle diffraction-pattern lines projected on surface 28, in a manner to be described.

An arcuate cradle 36 in the detector is rigidly attached to and formed with plate 26, and supported a selected distance therefrom, by a spacer arm 38 connecting the right side regions of the plate and cradle as shown. The cradle is adapted to be placed against a muscle or muscle region which is being illuminated, to position the plate a selected distance from the muscle-illumination region. The cradle includes a central opening 40 which is longitudinally aligned, in a generally left-to-right direction in FIG. 1, with marking 30 on the viewing surface of plate 26. In a preferred detector construction, the distance between opening 40 and the viewing surface of the plate, i.e. line 30, is about 8 to 12 cm. Detector 20 can be constructed readily as a single-piece molded plastic article, and preferably can be treated, e.g., by autoclaving to sterilize it before use.

It is assumed, for purposes of the present discussion, that muscle 16 in FIG. 1 has been detached from one of its skeletal connections, for example bone 12, and that the method of the invention is to be used in placing muscle 16 in an optimal-length condition as part of a surgical procedure for reattaching the muscle to the bone. According to one set-up procedure, a small bundle of fibers, which are indicated at 16a in FIG. 2, are carefully tweezed away from the bulk of the muscle, and held separated therefrom by pins, such as pin 42. The thickness of the illuminated bundle is preferably between about 0.5 to 2 millimeters. The end of probe 24 is then placed directly against or under the bundle for illumination of a segment 16b of the fiber bundle. It is noted that the overall change in length of the separated bundle is so slight with respect to the bulk muscle, that no appreciable distortion in length measurement occurs.

In a second set-up procedure, the probe is inserted into an outer layer of the muscle and pushed through this layer until a good diffraction pattern is observed, such occurring when the probe is positioned to illuminate a thin sheet of bundles. Typically the end of the probe will be within 0.5 to 2 mm from the far side of the muscle when a good diffraction pattern is first observed. The illuminated portion of the muscle is also referred to as a bundle segment.

Completing the description of the illuminating set-up procedure, detector 22 is placed against the other side of the illuminated bundle segment and positioned laterally thereon such that the projection of coherent light from the probe through the segment is directed through opening 40 against the viewing surface of plate 26.

It is known from earlier work by the inventors and others that cardiac and skeletal muscle, when illuminated by a monochromatic light source, produce a diffraction pattern which is related to the spacing between the regular light and dark striations (A and I bands) in the sarcomere units making up the muscle fiber. That is, the muscle-fiber striations act as a diffraction grating to produce a diffraction pattern which gives a precise indication of A-I band striation spacing, or sarcomere length. In its simplest form, the equation used for calculating the sarcomere length from the fraction line spacing is given by the equation:

$$\text{sarcomere length } (S.L.) = N \times \frac{L}{\sin a},$$

where N is the diffraction band order number, L is the wavelength of illuminating light and a is the angle of diffraction. This equation is used in calibrating markings, such as markings 32, in arbitrary sarcomere-length units, as a function of the distance between the projections of the zero-order and first-order diffraction lines on the viewing screen, when the screen is placed a selected distance from the illuminated muscle and the zero-order diffraction line is aligned with marking 30.

FIG. 2 shows a zero order diffraction line 44 and the two symmetrical first-order lines 46, 48 in a diffraction pattern produced by illuminating segment 16b with monochromatic light, it being understood that the diffraction pattern contains higher-order diffraction lines which are not shown in the figure. In practicing the invention, the position of the detector is adjusted, after its initial placement, so that the zero order diffraction line 44 is coincident with marking 30 on plate 26. The distance between the zero- and first-order diffraction lines, as determined from the marking position of the first-order diffraction line, then provides a direct measure of muscle sarcomere length, in arbitrary length units (corresponding to actual-length units at a defined wavelength of illuminating light.)

The relationship between muscle length (on stretching) and measured sarcomere length was examined in several experiments performed in support of the present application. In a first experiment, the sarcomere length in the extensor digitorum longus (EDL) muscle in rat was examined as a function of stretching produced by changes in skeletal joint angle. The EDL muscle, which runs along the shin region of the hind leg in the rat, becomes more stretched as the ankle joint angle between the ankle and the leg increases from a minimum angle of about 70° to a maximum flexing of about 175°, corresponding to the type of muscle stretching which would occur in muscle 16 illustrated in FIG. 1, as the interior angle of joint 14 is increased. Sarcomere length was determined, in accordance with the foregoing description of the invention, by isolating a small bundle of fibers on the outer surface of the EDL muscle, as illustrated in FIG. 2, and illuminating this bundle with a monochromatic light source, also as shown in FIG. 2, to produce a muscle diffraction pattern of the type described above. Detector 22 was used to measure the sarcomere length, in arbitrary length units, as described above, and these measured lengths were converted to actual-length values by correcting for the actual wavelength of illuminating light. Initially, the sarcomere length was measured with the leg in a neutral condition, at which the joint angle is approximately 150°. The leg was then moved to a maximally bent condition of 175°, then bent progressively toward the smaller joint angles shown in the left-hand column in Table I below. The measured muscle sarcomere lengths are shown in the right-hand column in Table I. As seen, sarcomere length increased in a substantially linear fashion with increasing joint angle. Following the test, the animal was removed from the surgical setting for a short time, then returned to the setting, and a second set of measured sarcomere length values determined at each of the above joint angles; this procedure was repeated a third time. The measured sarcomere lengths at each joint angle were substantially the same in each of the three tests, indicating good repeatability of sarcomere length measurement according to the invention. A similar experiment to determine sarcomere length as a function of joint angle was performed on rabbit EDL muscle and rabbit Tibialis Anterior muscle, with substantially the same results. That is, the sarcomere length measured at the neutral joint angle was about 2.7 and varied substantially linearly as the joint angle was increased or decreased from the neutral position.

TABLE I

| Joint Angle | Measured Sarcomere Length ($\mu$m) |
|---|---|
| 175° | 2.92 |
| 150° | 2.77 |
| 140° | 2.69 |
| 130° | 2.51 |
| 115° | 2.31 |
| 105° | 2.20 |
| 100° | 2.11 |
| 90° | 2.09 |

In practicing the method of the present invention, it is, of course, important for the surgeon to know the sarcomere length which corresponds to the optimal length of the muscle being surgically reattached. For most surgical procedures, the optimal length will be the length in the muscle before its detachment, with the joint in a neutral position. For many skeletal muscles in both humans and in veterinary animals, the sarcomere-length values of muscles in their neutral have been measured, and are typically about 2.7 microns. Thus, in many instances the surgeon can achieve an optimal tension in a muscle to be reattached by stretching the muscle until this sarcomere spacing is achieved. Where possible, however, the surgeon will preferably determine actual sarcomere length in the muscle before its surgical detachment, at one or more joint angles, to more precisely establish the relationship between joint angle, sarcomere length and optimal muscle length. The procedure for determining sarcomere length as a function of joint angle in a normally attached muscle which has been described above with reference to experimental animal muscles is generally applicable to human orthopaedic surgery.

In carrying out a muscle reattachment operation, the surgeon illuminates the detached muscle, such as muscle 16, with a coherent light, in the manner described above, to produce a diffraction pattern which is visualized on the viewing screen of detector 22, which is positioned to align the zero-order diffraction line at the zero-point line on the plate. The surgeon then stretches the muscle to adjust the overall muscle length until the first-order diffraction line falls on a marking corresponding to the selected sarcomere length. That is, the muscle length is adjusted until an optimal length, as evidenced by predetermined diffraction-line spacing, is achieved. The surgical reattachment of the muscle is made with the muscle in this optimal length condition.

Figure 3:
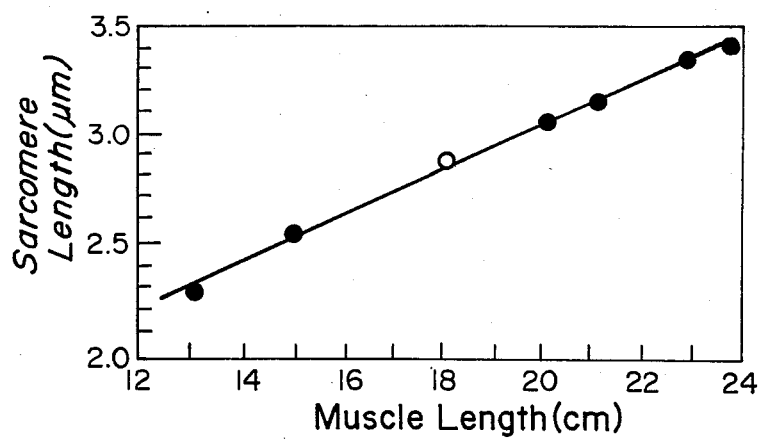
FIG. 3 is a graph of sarcomere length as a function of muscle length determined in accordance with the present invention.

An application of the method of the invention to a surgical operation to repair a chain-saw injury, in which the subject's upper-wrist muscles were severed, will now be described. The surgical repair of this injury involved a tendon-transfer procedure to replace the severed upper-wrist muscle with a healthy lower-wrist muscle. The optimal tension in the transferred lower-wrist muscle was determined, as described herein, with the wrist in a neutral position, at which the muscle had a length of 18 centimeters and a measured sarcomere length of 2.75 microns. The lower-wrist muscle was then surgically detached and its sarcomere length at a number of different lengths was determined in accordance with the procedures outlined above. FIG. 3, shows the measured sarcomere length as a function of muscle length in the muscle-length range between 13 and 24 centimeters. The sarcomere length value at 18 centimeters, shown by an open circle in FIG. 3 was determined before the muscle was removed from its lower-wrist connections. The excised muscle was then surgically reattached at a suitable anatomical connection site on the upper wrist and stretched until the desired sarcomere length value of about 2.8 was measured, in accordance with the invention. With the wrist in its neutral position, the other end of the transferred muscle was then reattached to complete the operation.

Figure 4:
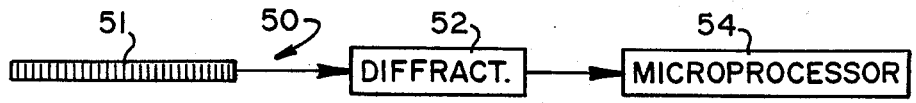
FIG. 4 is a block diagram of components of an alternative type of diffraction-line detector which can be used in practicing the present invention.

FIG. 4 shows another embodiment of a detector 50 intended for use in practicing the invention. Detector 50 includes a multi-element device 51 containing an array of photodiodes on which the muscle diffraction pattern is imaged. A preferred photodiode array (PDA) contains a linear array of 256 elements which provides an analog output of 256 points of light-intensity data which may be digitized and stored with a spatial resolution of up to 5 nanometers per sarcomere. One preferred array device is available from Reticon (Redwood City, Calif.). The PDA is connected, through a diffractometer 52, to a microprocessor 54. The diffractometer clocks the PDA, amplifies its analog data output, and generates the required timing and control pulses for computer acquisition. The microprocessor is designed conventionally for data acquisition, storage, display, analysis and experimental processing and control. In particular, the microprocessor is designed to receive digitized data from the the diffractometer and convert this to a sarcomere-length output data display which can be read by the surgeon during a muscle attachment surgical operation. The design of the microprocessor and its interface with the diffractometer would be well known to one skilled in the art. Detector 50 also includes a frame (not shown), such as the frame associated with detector 22, for holding and positioning the PDA at a selected distance from the illuminated muscle. The electronic detector can be readily constructed as a compact, easily portable unit with a simple LED display.

From the foregoing, it can be appreciated how various objects of the invention are met. The present invention overcomes the problems currently encountered when a surgeon must estimate the tension present in a muscle. Instead of relying on the subjective feel of a muscle, the surgeon can use the present method to obtain an accurate measurement of sarcomere spacing within the muscle, and thus obtain an accurate measure of optimal length and maximum tension in a detached muscle.

The present invention is easily carried out without interfering with the normal surgical procedures in a muscle-reattachment operation. The equipment used in practicing the invention is simple and, in the case of the viewing-screen detection, inexpensive. The method is generally applicable to orthopaedic surgery in humans and veterinary animals where surgical reattachment is required.

While a preferred embodiment of the invention has been described herein, it will be appreciated that various changes and modifications can be made without departing from the spirit of the invention.

What is claimed is:

1. In a surgical setting, where a detached, striated muscle is to be attached between anatomical connection sites, a method for placing the muscle at an optimal length when said muscle attachment is made surgically, comprising the steps of illuminating a bundle of fibers from said muscle with monochromatic light, by said illumination, producing a diffraction pattern including a plurality of lines resulting from the diffraction of said light by the fibers of said bundle, determining the distance between two of said lines in said diffraction pattern, comparing said distance with a predetermined diffraction line distance corresponding to said optimal length, adjusting the muscle length to reduce the diffraction between said determined distance between said two lines and said predetermined diffraction line distance, and repeating said steps of determining, comparing, and adjusting until the difference between said determined distance and said predetermined diffraction line distance is less than a preselected value.

2. The method of claim 1, wherein said illuminating is performed by a laser opticla fiber probe placed adjacent to said fiber bundle.

3., The method of claim 1, wherein said step of illuminating includes separating said bundle of fibers from the bulk of said muscle.

4. The method of claim 2, wherein said illuminating includes pushing the probe through an outer layer of the muscle until a muscle diffraction pattern becomes visible.

5. The method of claim 1, wherein said step of determining the distance between two lines includes providing a detector for detecting diffraction line spacings, placing the detector at a predetermined distance from said illuminated bundle of fibers, and determining the distance with the detector.

6. The method of claim 5, wherein said detector visually measures the distance between said two lines.

7. The method of claim 5, wherein the detector includes an array of photodiode elements and a microprocessor connected thereto for calculating the distance between diffraction lines impinging on said array, and from said calculated distance, calculating muscle sarcomere spacing.

8. The method of claim 5, in which the muscle to be reattached is first detached from its normal attachment site, wherein the method further includes the step of determining the predetermined diffraction line distance corresponding to said optimal length in the muscle, prior to its detachment, by adjusting said muscle to said optimal length and performing said illuminating, and determining steps.

* * * * *

UNITED STATES PATENT AND TRADEMARK OFFICE
CERTIFICATE OF CORRECTION

PATENT NO. : 4,570,641
DATED : February 18, 1986
INVENTOR(S) : Richard L. Lieber, et al.

It is certified that error appears in the above-identified patent and that said Letters Patent is hereby corrected as shown below:

Column 2, line 44, "anatomica" should be --anatomical--.

Column 8, line 11, in Claim 1, "diffraction", should be --difference--.

Column 8, line 20, in Claim 2, "opticula" should be --optical--.

Signed and Sealed this

Seventeenth Day of June 1986

[SEAL]

Attest:

DONALD J. QUIGG

Attesting Officer

Commissioner of Patents and Trademarks